United States Patent
Miraki et al.

(10) Patent No.: US 10,188,376 B2
(45) Date of Patent: Jan. 29, 2019

(54) TISSUE RETRACTOR

(71) Applicant: Edwards Lifesciences Corporation, Irvine, CA (US)

(72) Inventors: Manouchehr A. Miraki, Laguna Hills, CA (US); Kevin K. Dang, Garden Grove, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 15/803,632

(22) Filed: Nov. 3, 2017

(65) Prior Publication Data

US 2018/0055505 A1    Mar. 1, 2018

Related U.S. Application Data

(63) Continuation of application No. 14/327,440, filed on Jul. 9, 2014, now Pat. No. 9,808,231.

(Continued)

(51) Int. Cl.
  *A61B 1/32*    (2006.01)
  *A61B 17/02*    (2006.01)
  *A61F 2/24*    (2006.01)

(52) U.S. Cl.
  CPC ...... *A61B 17/0206* (2013.01); *A61B 17/0293* (2013.01); *A61B 2017/0237* (2013.01); *A61B 2017/0287* (2013.01); *A61F 2/2427* (2013.01)

(58) Field of Classification Search
  CPC combination set(s) only.
  See application file for complete search history.

(56) References Cited

U.S. PATENT DOCUMENTS

| 1,810,466 A | 6/1931 | Deutsch |
| 2,070,670 A | 2/1937 | Marshall |

(Continued)

FOREIGN PATENT DOCUMENTS

| WO | 9732514 A2 | 9/1997 |
| WO | 9901696 A1 | 1/1999 |

OTHER PUBLICATIONS

Robinson, et al., "Minimally Invasive Coronary Artery BypassGrafting: A New Method Using an AnteriorMediastinotomy," J. Card. Surg., 1995; 10:529-536.

(Continued)

*Primary Examiner* — Sameh Boles
(74) *Attorney, Agent, or Firm* — Rick Cates, Esq.

(57) ABSTRACT

A surgical site retractor is configured to retract tissue, such as in an intercostal procedure. The retractor may be formed from non-radiopaque material for improved monitoring via X-ray imaging. The retractor may have a rigid retractor and a soft tissue retractor, where the rigid retractor has a plurality of legs and the soft tissue retractor extends between the legs to prevent soft tissue from extending between said legs. The retractor may have a bendable arm with an implement holder, such as distal cuff or clip adapted to resiliently hold an implement such as a tube of an elongated port-access device. A method involves partly installing the surgical site retractor, expanding the surgical site retractor, deploying the surgical implement from outside the body through the incision and into the patient, resiliently capturing the implement with the holder of the arm, and bending the arm to hold the implement in a desired position.

20 Claims, 15 Drawing Sheets

Related U.S. Application Data

(60) Provisional application No. 61/844,405, filed on Jul. 9, 2013.

(56) References Cited

U.S. PATENT DOCUMENTS

| | | |
|---|---|---|
| 2,305,289 A | 12/1942 | Coburg |
| 2,701,562 A | 2/1955 | Michael et al. |
| 2,739,587 A | 3/1956 | Scholl |
| 3,111,943 A | 11/1963 | Orndorff |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 3,416,520 A | 12/1968 | Creager, Jr. |
| 3,473,528 A | 10/1969 | Mishkin et al. |
| 3,523,534 A | 8/1970 | Nolan |
| 3,638,644 A | 2/1972 | Reick |
| 3,641,332 A | 2/1972 | Reick et al. |
| 3,768,477 A | 10/1973 | Anders et al. |
| 3,841,332 A | 10/1974 | Treacle |
| 3,863,639 A | 2/1975 | Kleaveland |
| 4,155,355 A | 5/1979 | Yamamoto |
| 4,188,945 A | 2/1980 | Wenander |
| 4,188,975 A | 2/1980 | Bauer |
| 4,274,398 A | 6/1981 | Scott, Jr. |
| 4,387,706 A | 6/1983 | Glass |
| 4,412,532 A | 11/1983 | Anthony |
| 4,421,107 A | 12/1983 | Estes et al. |
| 4,430,991 A | 2/1984 | Darnell |
| 4,434,791 A | 3/1984 | Darnell |
| 4,492,229 A | 1/1985 | Grunwald |
| RE32,021 E | 11/1985 | Scott, Jr. |
| 4,553,537 A | 11/1985 | Rosenberg |
| 4,560,832 A | 12/1985 | Bond et al. |
| 4,562,832 A | 1/1986 | Wilder et al. |
| 4,726,356 A | 2/1988 | Santilli et al. |
| 4,777,943 A | 10/1988 | Chvapil |
| 4,984,564 A | 1/1991 | Yuen |
| 5,005,108 A | 4/1991 | Pristash et al. |
| 5,052,374 A | 10/1991 | Alvarez-Jacinto |
| 5,054,906 A | 10/1991 | Lyons, Jr. |
| 5,159,921 A | 11/1992 | Hoover |
| 5,213,114 A | 5/1993 | Bailey, Jr. |
| 5,231,974 A | 8/1993 | Giglio et al. |
| 5,263,922 A | 11/1993 | Sova et al. |
| 5,351,680 A | 10/1994 | Jung |
| 5,366,478 A | 11/1994 | Brinkerhoff et al. |
| 5,391,156 A | 2/1995 | Hildwein et al. |
| 5,441,044 A | 8/1995 | Tovey et al. |
| 5,452,733 A | 9/1995 | Sterman et al. |
| 5,460,170 A | 10/1995 | Hammerslag |
| 5,476,510 A | 12/1995 | Eberhardt et al. |
| 5,520,610 A | 5/1996 | Giglio et al. |
| 5,520,611 A | 5/1996 | Rao et al. |
| 5,524,644 A | 6/1996 | Crook |
| 5,556,417 A | 9/1996 | Sher |
| 5,571,215 A | 11/1996 | Sterman et al. |
| 5,582,577 A | 12/1996 | Lund et al. |
| 5,613,751 A | 3/1997 | Parker et al. |
| 5,613,937 A | 3/1997 | Garrison et al. |
| 5,618,096 A | 4/1997 | Parker et al. |
| 5,649,550 A | 7/1997 | Crook |
| 5,656,013 A | 8/1997 | Yoon |
| 5,681,341 A | 10/1997 | Lunsford et al. |
| 5,785,649 A | 7/1998 | Fowler, Jr. |
| 5,810,721 A | 9/1998 | Mueller et al. |
| 5,888,247 A | 3/1999 | Benetti |
| 5,967,970 A | 10/1999 | Cowan et al. |
| 6,048,309 A | 4/2000 | Flom et al. |
| 6,142,935 A | 11/2000 | Flom et al. |
| 6,176,824 B1 | 1/2001 | Davis |
| 6,193,652 B1 | 2/2001 | Berky et al. |
| 6,241,658 B1 | 6/2001 | Goodrich |
| 6,254,534 B1 | 7/2001 | Butler et al. |
| 6,478,728 B1 | 11/2002 | Wright |
| 6,613,952 B2 | 9/2003 | Rambo |
| 6,723,044 B2 | 4/2004 | Pulford et al. |
| 6,814,700 B1 | 11/2004 | Mueller et al. |
| 7,008,377 B2 | 3/2006 | Beane et al. |
| 7,758,500 B2 | 7/2010 | Boyd |
| 8,348,998 B2 | 1/2013 | Pintor et al. |
| 2003/0060685 A1 | 3/2003 | Houser et al. |
| 2003/0095781 A1 | 5/2003 | Williams |
| 2005/0215863 A1 * | 9/2005 | Ravikumar ............ A61B 17/02 600/204 |
| 2006/0074484 A1 | 4/2006 | Huber |
| 2007/0112422 A1 | 5/2007 | Dehdashtian |

OTHER PUBLICATIONS

Landreneau, et al., "Video-Assisted Thoracic Surgery: Basic Technical Concepts and Intercostal Approach Strategies," Ann. Thoracic Surg., 1992; 54:800-7.

Lone Star Medical Products, Inc., The Lone Star Retractor System brochure/catalog, pp. 1-32, Oct. 2015.

\* cited by examiner

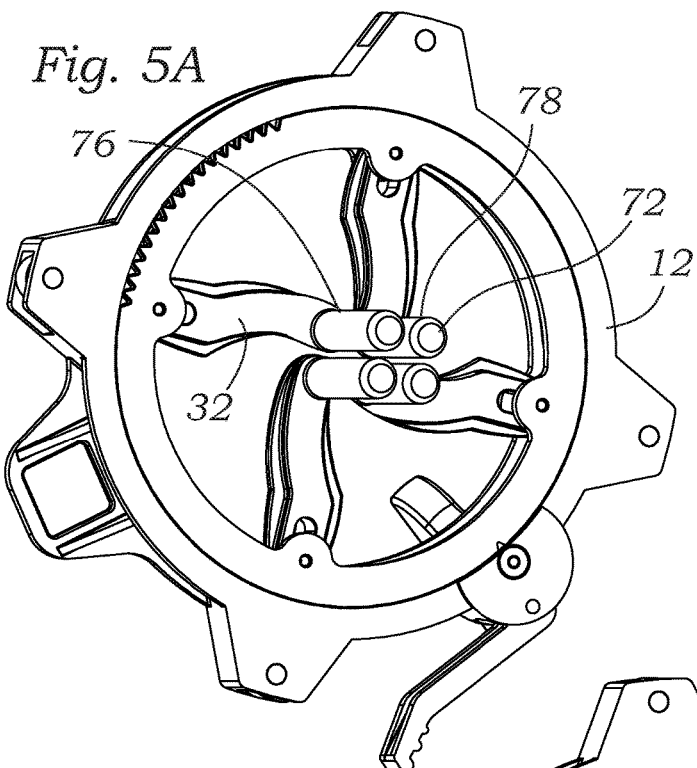
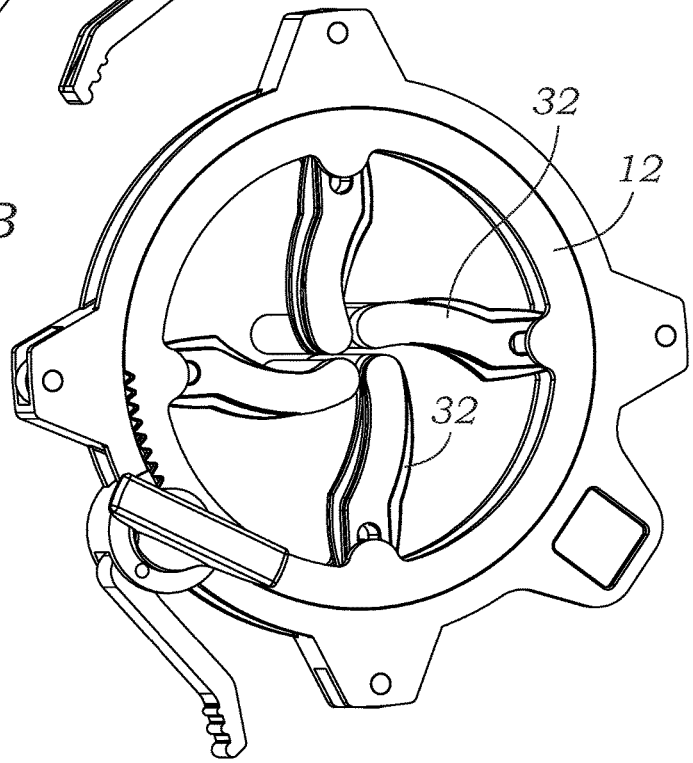

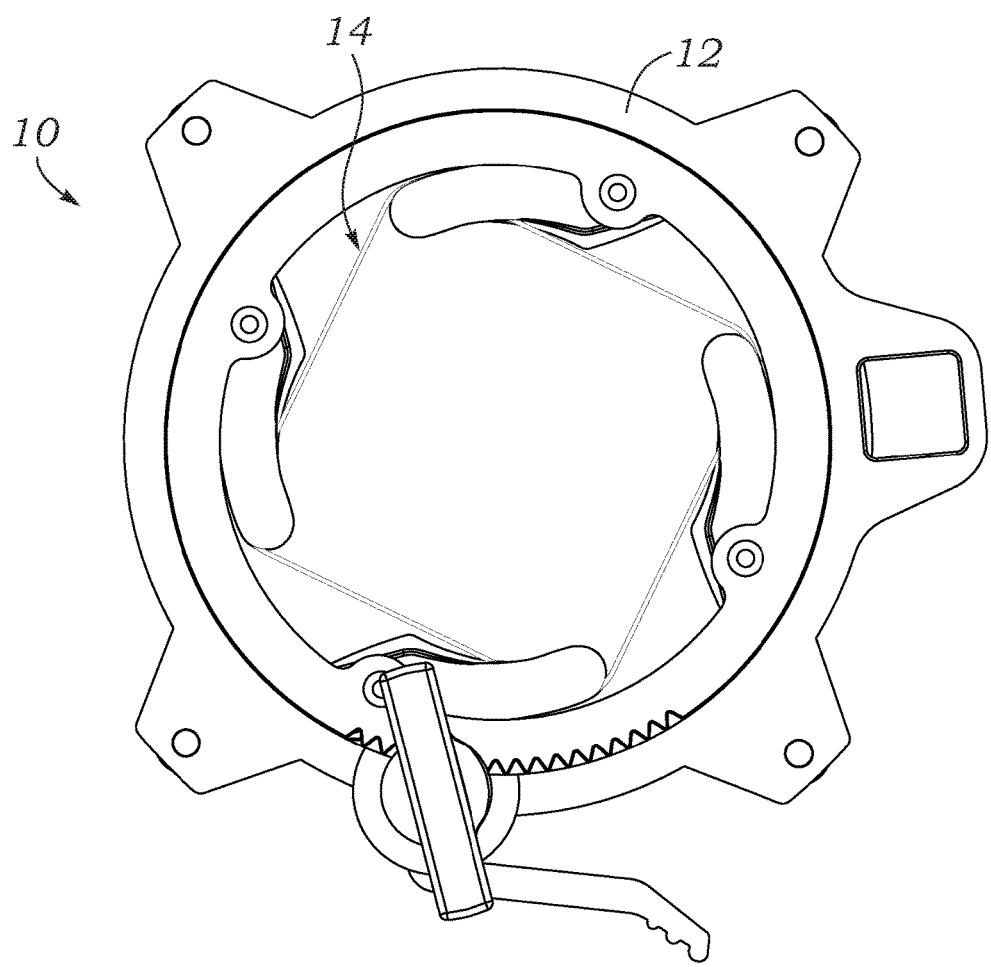

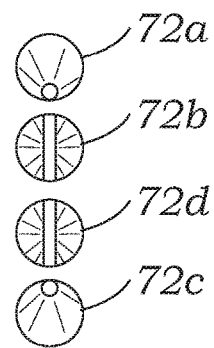
Fig. 8A
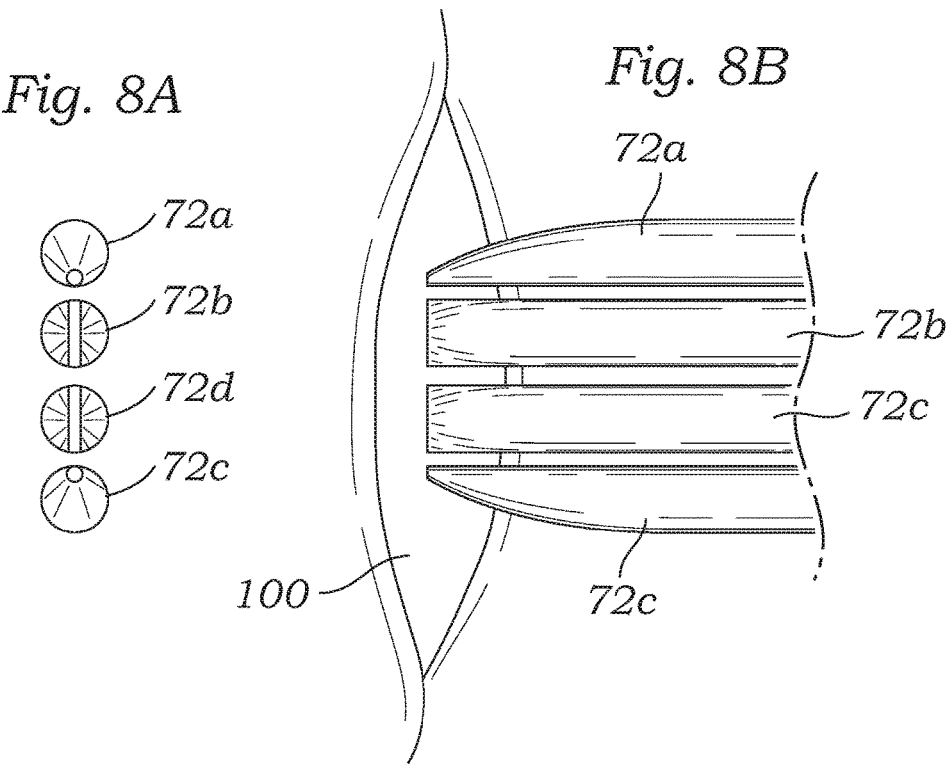
Fig. 8B
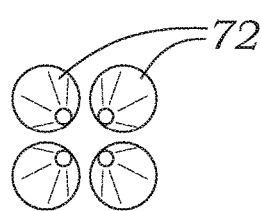
Fig. 9A
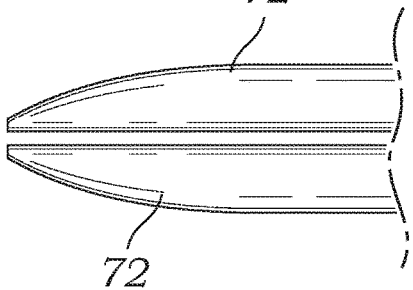
Fig. 9B

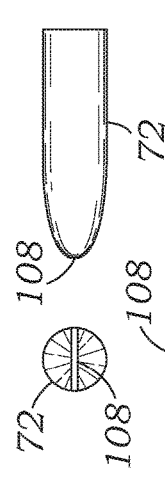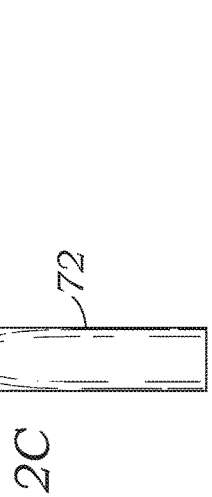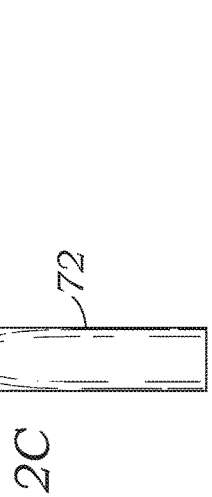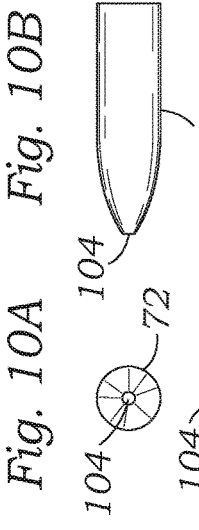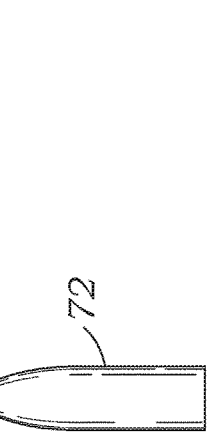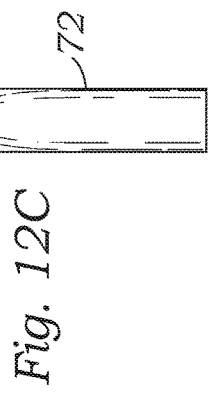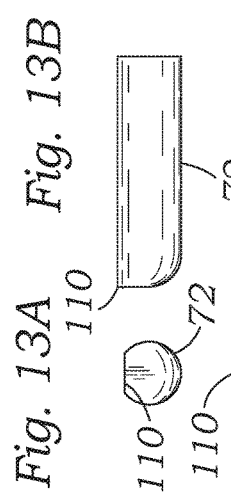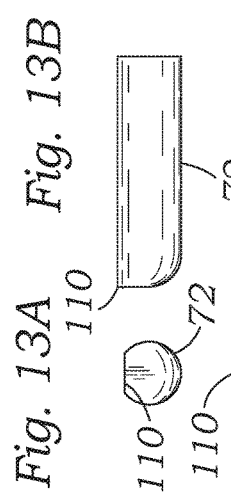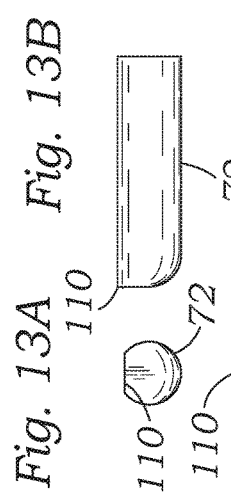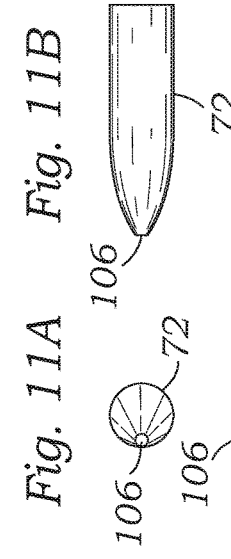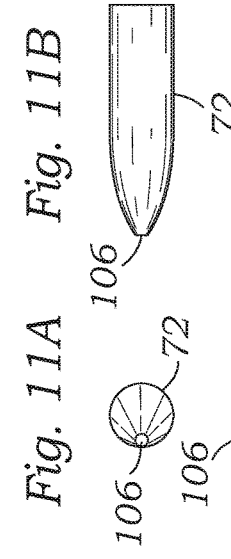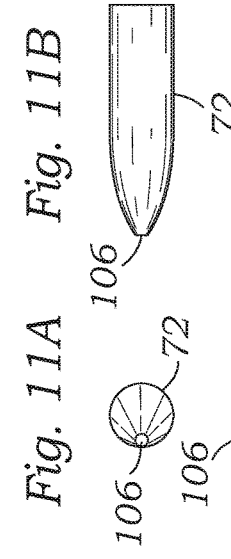

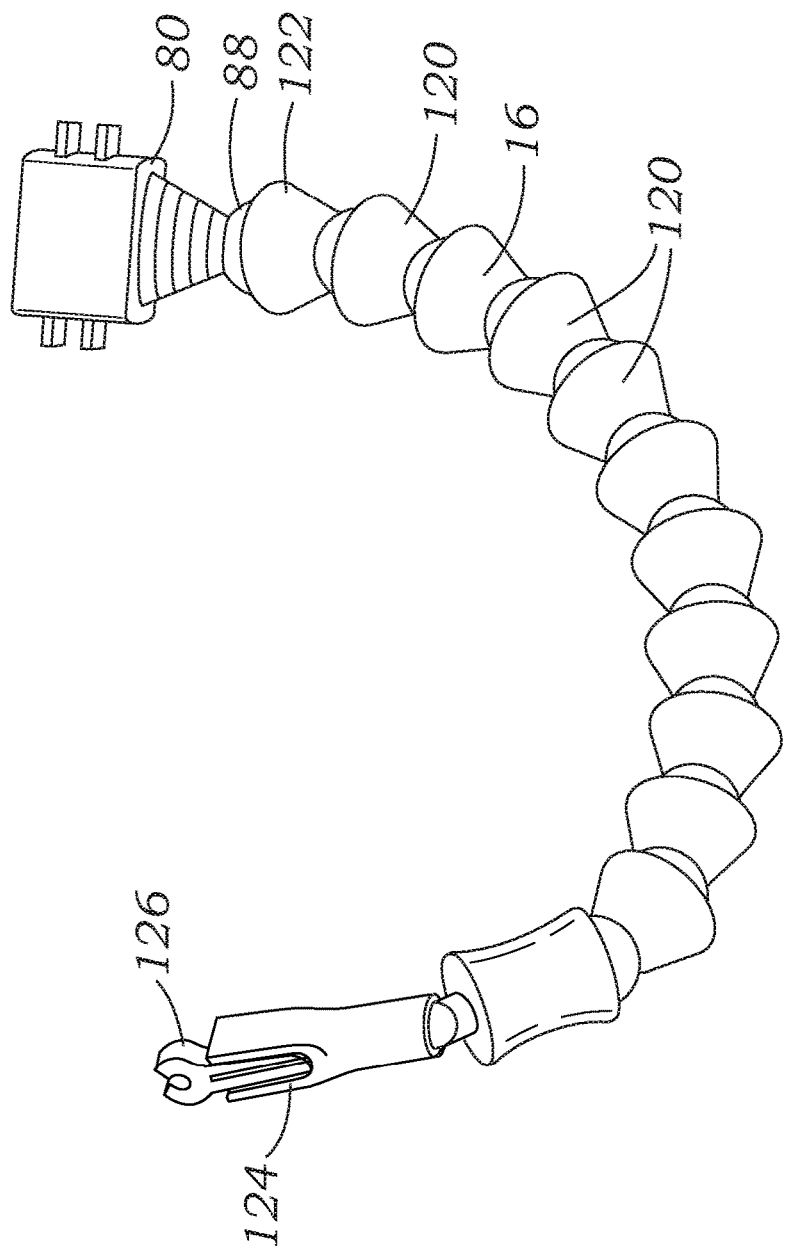

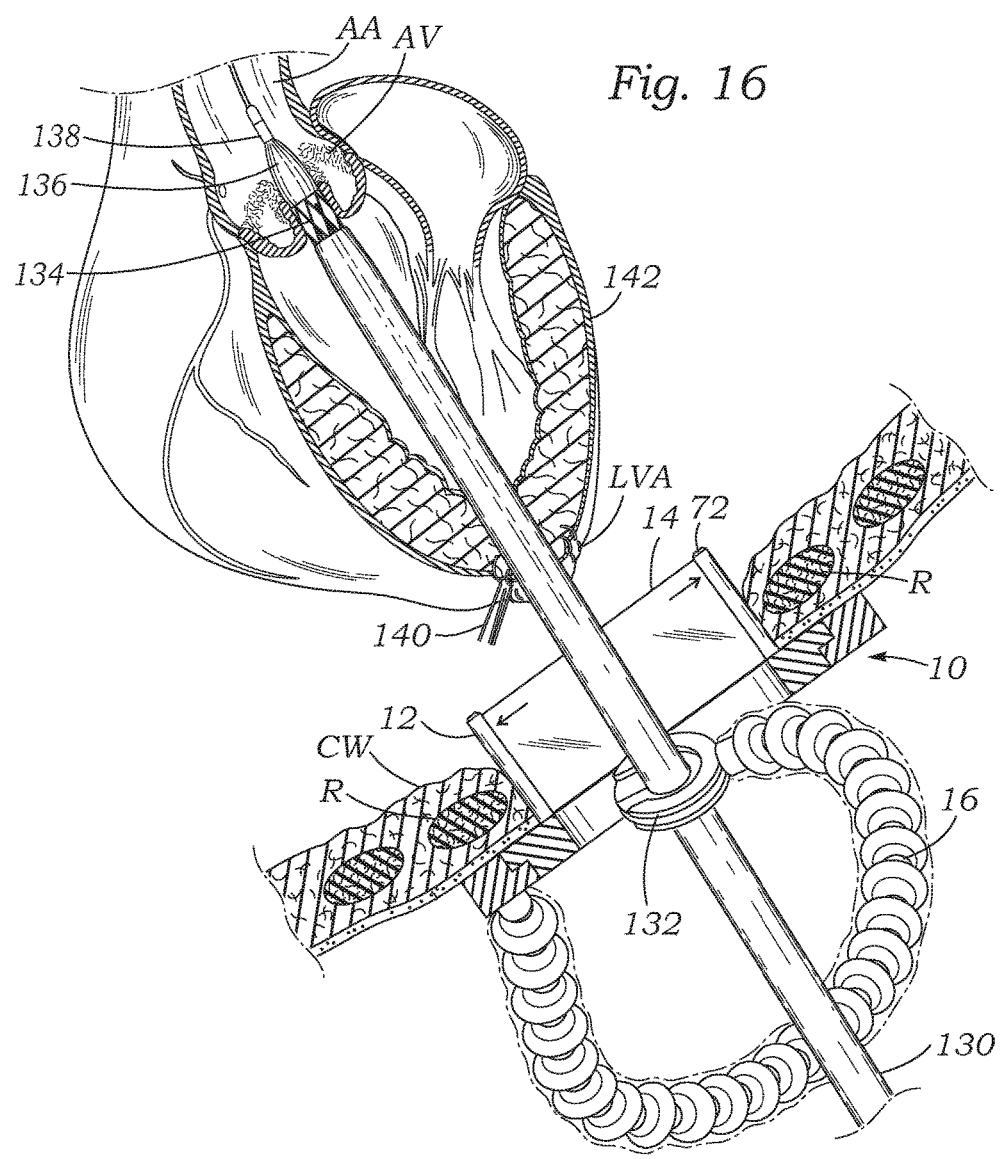

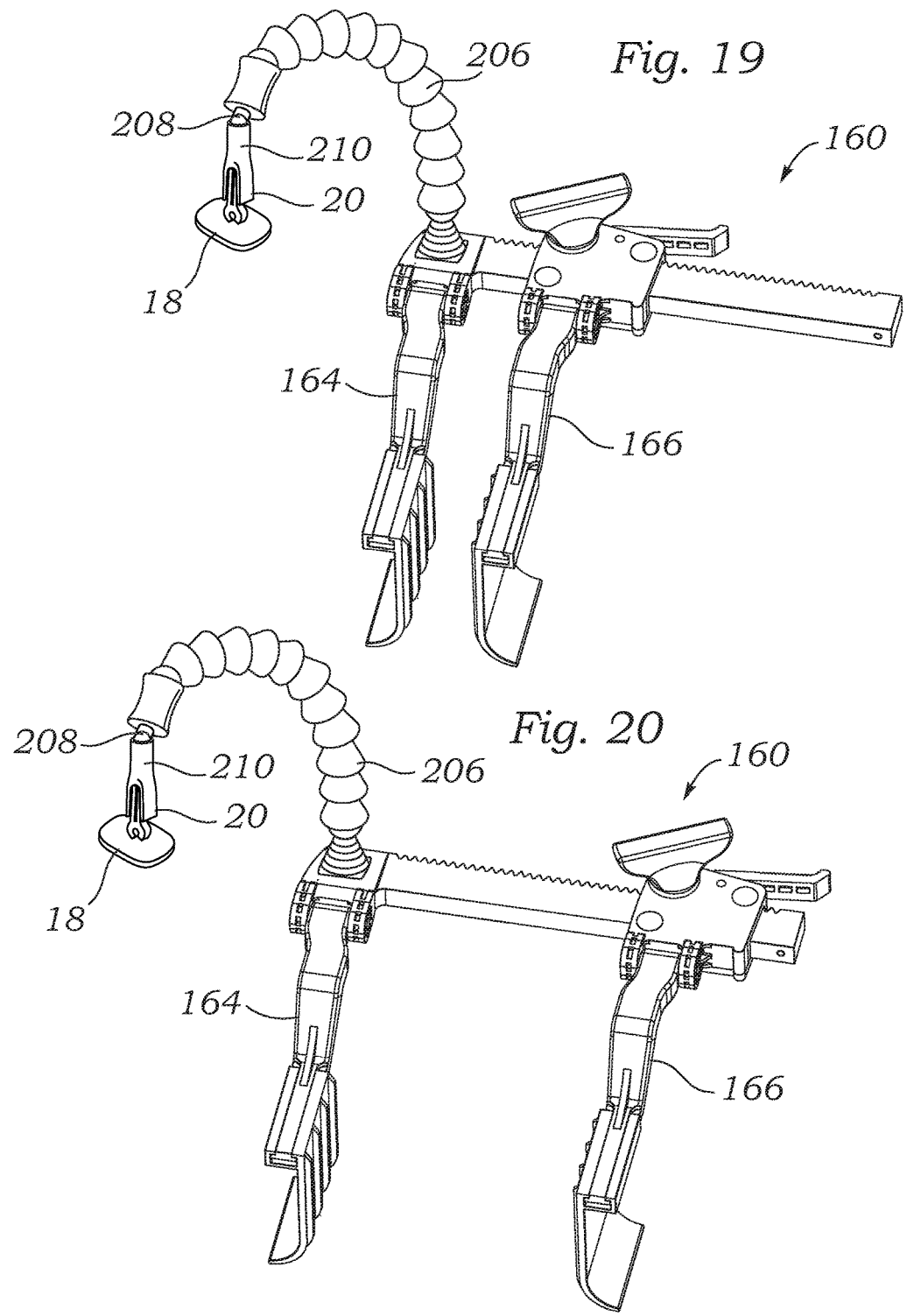

TISSUE RETRACTOR

CROSS REFERENCE TO RELATED APPLICATIONS

This application is a continuation of U.S. application Ser. No. 14/327,440, filed Jul. 9, 2014, now, U.S. Pat. No. 9,808,231, which claims the benefit of U.S. Application No. 61/844,405, filed Jul. 9, 2013, the entire contents all of which are incorporated by reference herein.

FIELD OF THE INVENTION

The present invention relates generally to methods and devices for minimally invasive and less invasive surgical access. More particularly, the present invention provides retractors for tissues and methods for their use to provide access into body cavities, such as during a cardiac procedure.

BACKGROUND OF THE INVENTION

Heart valve disease continues to be a significant cause of morbidity and mortality, resulting from a number of ailments including rheumatic fever and birth defects. Recent statistics show that valvular heart disease is responsible for nearly 20,000 deaths each year in the United States, and is a contributing factor in approximately 42,000 deaths. Currently, the primary treatment of aortic valve disease is valve replacement. Worldwide, there are approximately 300,000 heart valve replacement surgeries performed annually.

Coronary artery disease also remains a leading cause of morbidity and mortality and manifests in a number of ways. For example, disease of the coronary arteries can lead to insufficient blood flow resulting in the discomfort and risks of angina and ischemia. In severe cases, acute blockage of coronary blood flow can result in myocardial infarction, leading to immediate death or damage to the myocardial tissue.

A number of interventional approaches have been developed for treating heart valve and coronary artery disease. For instance, annuloplasty rings have been developed in various shapes and configurations over the years to correct mitral regurgitation and other conditions which reduce the functioning of the valve. Heart valve replacement may be indicated when there is a narrowing of a native heart valve, commonly referred to as stenosis, or when the native valve leaks or regurgitates, such as when the leaflets are calcified. When replacing the valve, the native valve may be excised and replaced with either a biologic or a mechanical valve. Coronary blockage can often be treated endovascularly using techniques such as balloon angioplasty, atherectomy, or stents.

Most interventional techniques are conducted under general anesthesia and require that the patient's sternum be opened and the chest be spread apart to provide access to the heart. The first 2-3 days following surgery are spent in an intensive care unit where heart functions can be closely monitored. The average hospital stay is between 1 to 2 weeks, with several more weeks to months required for complete recovery. While often very effective, the use of open-heart surgery to perform cardiac procedures is a highly traumatic to the patient.

Recently, minimally invasive surgical techniques and procedures to perform coronary artery bypass grafting (CABG) and other traditionally open-chest cardiac surgical procedures are gaining acceptance. A wide variety of laparoscopic, arthroscopic, endovascular, and other surgical therapies have been developed. These procedures generally utilize trocars, cannulas, catheters, or other tubular sheaths to provide an artificial lumen, through which specialized tools are inserted and manipulated by the surgeon.

Some researchers propose implanting prosthetic heart valves at the aortic annulus using a direct-access transapical (through the left ventricular apex) approach (e.g., U.S. Patent Publication No. 2006-0074484). The left ventricular apex LVA is directed downward, forward, and to the left (from the perspective of the patient). The apex typically lies behind the fifth left intercostal space (or between the fourth and fifth), 8 to 9 cm from the mid-sternal line, and about 4 cm below and 2 mm to the medial side of the left mammary papilla. Access to the left ventricle may therefore be attained through an intercostal incision positioned over the fifth left intercostal space. Such an approach is often termed a "mini-thoracotomy," and lends itself to surgical operations on the heart carried out using one or more short tubes or "ports"—thus, the operations are often referred to as "port-access" procedures.

Dehdashtian in U.S. Patent Publication No. 2007-0112422 discloses a port-access delivery system for transapical delivery of a prosthetic heart valve including a balloon catheter having a steering mechanism thereon that passes through an access device such as an introducer. The surgeon forms a puncture in the apex with a needle, advances a guidewire, then a dilator, and finally the introducer. Edwards Lifesciences sells the Sapien™ Heart Valve that may be inserted transapically with the Ascendra™ delivery system, much like the system disclosed in Dehdashtian.

Often, direct- or port-access techniques are conducted or proposed for off-pump, or beating heart procedures. The advantages of eliminating open-heart procedures and cardiopulmonary bypass are evident. Challenges remain in retracting and stabilizing tissue, and in providing improved visualization, during these procedures. During port-access procedures, it can be helpful for a retractor to create an opening through which surgeons can not only advance medical devices but which also provide a visualization area of sufficient size. Many current retractors provide retraction in only two opposing directions, which can limit the size of the opening provided. Other retractors have radiopacity that prevents a surgeon from seeing the desired field of view beyond the retractor via X-ray or similar techniques. An additional issue is the need to hold medical devices during a procedure. For example, during ring or valve replacement, the ring and/or valve is often secured to a handle for delivery through the access port. During the procedure, this handle is typically held within the access port at a desired position by a second operator who assists the main surgeon conducting the procedure. The surgeon typically takes needle and suture one at a time and goes around the ring/valve perimeter in order to secure the ring/valve within the native valve annulus.

During many surgeries, such as valve surgeries, there is a need for a retractor that can create an opening through which surgeons can operate, which may include retraction of bone as well as soft tissues. In some cases there is also a need for the retractor to create a sufficient visualization area for the surgeon to visualize the operating area within the patient. Some current retractors retract the tissue in limited directions which can limit the size of the opening created (thus limiting the access and/or visualization). Other retractors have may have excessively radiopaque materials that may prevent X-ray visualization of the field of view beyond the radiopaque retractor.

Another potential issue during surgeries such as heart valve repair (e.g., valve ring deployment) and/or heart valve replacement procedures is the number of personnel required to conduct the procedure. For example, in a valve ring or prosthetic valve deployment, the valve ring or prosthetic valve is typically secured to a handle that must be held in place while the main surgeon stitches (e.g., with needle and suture passing around the valve/ring perimeter to secure the prosthetic in place) or otherwise secures the valve ring/prosthetic valve in its desired position in the patient. Typically a second operator is required to hold the valve ring/prosthetic valve in place via the handle during the stitching process. deployed from a valve ring or valve the There is a need for improved retractors capable of creating a port opening with improved visualization while eliminating the need for a second operator to hold the handle of the deployment device. The current invention satisfies these needs.

SUMMARY OF THE INVENTION

Preferred embodiments of the present application provide a retractor configured to create a relatively large access opening through a relatively small incision, with the goal of improving visualization. The retractor may be formed from non-radiopaque materials to improve visualization of the field of view beyond the retractor when X-ray visualization is used. The retractor may include a flexible/bendable arm that can hold the valve/ring (via valve/ring holder handle) to reduce the number of personnel required for the procedure. In particular, the present application discloses retractors that assist a port-access heart valve ring delivery system and/or prosthetic heart valve delivery system for delivery of a same through the heart wall to a native valve site.

A surgical retractor according to the invention may be formed largely, or entirely, of non-radiopaque materials for improved X-ray imaging during the procedure.

The surgical retractor according to embodiments of the invention may include one or more arms capable of being bent into and retaining a variety of shapes attaches to the main frame extending away from the base. The arm may include various holders for surgical implements, such as a cuff attached to the arm at a distal end thereof, the cuff having a stiff C-shaped partial ring and a flexible gasket held across an area defined within the C-shaped partial ring. The gasket defines a slit directed toward an open mouth of the C-shaped partial ring, the open mouth being sized larger than an elongated port-access device having a tube such that the cuff can be pressed around the tube, or vice versa, with the tube entering the slit and being resiliently held by the gasket. Other holders include grasping-style (i.e., vise-like) holders and snap-on connections.

Another aspect of the application is a rigid retractor and soft tissue retractor combination for assisting an intracardiac procedure through an incision. The rigid retractor may include 2, 3, 4, 5, 6, or more legs which, in the closed position, are positioned adjacent each other in a substantially central position, but when the retractor is opened the legs move apart to press hard tissue portions, such as ribs, apart. A soft tissue retractor may be positioned to cover the spacing between legs to prevent soft tissues from pressing between the spaces between the legs of the retractor.

A surgical site retractor according to an embodiment of the invention comprises a rigid retractor having a base defining a periphery having a size that enables it to be held against an exterior chest wall by the surgical site retractor and around a chest incision, a plurality of legs extending downwardly from the base, a gear or other assembly configured to move the legs from a substantially central position on the base and adjacent each other to a substantially non-central position where the legs are spaced apart from other and defining a periphery of an open space therebetween. The retractor may include a one or more arms attached to and extending away from the base and capable of being bent into and retaining a variety of shapes, with an implement holder secured to a distal end of each of the arms. The implement holder may be a cuff with a flexible gasket, or a clip-like clamping element, or similar grasping assemblies. The base may define a slightly concave lower contact face, and the base and gears and legs and other elements of the retractor may be formed predominantly from non-radiopaque materials. The legs may have various lengths (e.g., 0.25 to 4 inches, 0.5 to 3 inches, 2 to 3 inches, 1 to 3 inches, or more), and various diameters (or for legs with non-circular cross sections other thicknesses), e.g., between 0.1 and 0.8 inches. The retractor may have a soft tissue retractor secured to the legs, and the soft tissue retractor may comprise a flexible film extending between the legs and around the periphery defined by the legs. The soft tissue retractor may have a substantially continuous loop of flexible film defining a soft tissue retractor perimeter. A plurality of tubes may be secured to the continuous loop of film, each of the tubes extending at least partially across the loop of flexible film in a direction substantially perpendicular to the perimeter. The tubes may be configured to slidingly receive the legs, and may have a depth equal to the length of the legs. The soft tissue retractor may have a depth of 0.25 to 4 inches, 0.5 to 3 inches, 2 to 3 inches, 1 to 3 inches, or more.

A soft tissue retractor according to the invention may have a substantially continuous loop of flexible film, the continuous loop defining a perimeter (which may be between 4 and 12 inches or more in circumference, and may have a depth of between 1 and 3 inches or more), and a plurality of tubes secured to the continuous loop of film, each of the tubes extending at least partially across the loop of flexible film in a direction substantially perpendicular to the perimeter. Each of the tubes may define an inner lumen, which may have an inner diameter that may, for example, be between 0.1 to 0.8 inches. Each tube may have a length, which may be between 0.25 and 4 inches, 0.5 and 3 inches, 1 and 2 inches, 1 to 3 inches, or other lengths, depending on the particular application. The tube length may match the continuous loop depth. The continuous loop may be formed from a film of translucent or transparent material for improved visibility of the tissues being retracted and other aspects of the surgical site. The film may be a polymer film, such as polyurethane or equivalent thermoplastic elastomer, and may have various thicknesses, such as a thickness of 1 to 3 mm.

A further aspect described herein provides a combination of devices for performing an intracardiac procedure through an intercostal incision in a chest wall. The combination features a retractor that includes an arm attached to the base and capable of being bent into a variety of shapes and a cuff or other implement-holding element attached to the arm opposite the base. A port-access device having a tube sized to pass from outside the chest wall through the intercostal incision and through a puncture in the heart wall is resiliently held by the arm at a desired position. The surgical site retractor may have rigid elements (e.g., legs for spreading adjacent ribs) as well as a "soft" retractor that includes a material extending between retractor legs to prevent soft tissues from extending therebetween. The legs are sized to pass through the intercostal incision and expand therein to move adjacent ribs apart.

A method for performing an intracardiac procedure through an intercostal incision is described herein. The method includes: partly installing a surgical site retractor by extending legs thereof into a body opening such as an intercostal incision; moving the legs of the retractor apart from each other in order to engage and press adjacent ribs apart; deploying an implement through the incision, such as a port-access device having a tube, which may be deployed from outside the body through the incision and through a puncture in the heart wall; and capturing the port-access device via an implement-holding mechanism on a distal end of a bendable positioning arm attached to the base of the retractor.

The above method may include installing the retractor with a soft tissue retractor positioned over the legs, and expanding the soft tissue retractor when the legs of the retractor are moved to the open position.

Arms attached to and extending away from the retractors may be capable of being bent into and retaining a variety of shapes, and may have implement-holding elements such as a distal cuff or distal clip attached thereto opposite the base. The arms may be formed of segments secured in end-to-end fashion to form the arm, and may have a malleable element extending through aligned throughbores in the segments substantially the entire length of each arm. Additionally, a frictional interface tube may be sized to closely surround the malleable element and fit closely within the aligned throughbores. In one embodiment, the malleable element is a malleable tube and the frictional interface tube is an elastomer.

Another aspect of the present application is a combination of devices for performing an intracardiac procedure through a chest incision comprising a surgical site retractor for holding open the chest incision. A surgical retractor including a base having an arm extending therefrom is adapted to be positioned at least partially within the chest wall to expand same. The bendable arm attached to the base may be capable of being bent into a variety of shapes.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

Features and advantages of the present invention will become appreciated as the same become better understood with reference to the specification, claims, and appended drawings wherein:

FIGS. 5A-5B are bottom perspective and top views, respectively, of a rigid spreader retractor in a closed configuration according to an embodiment of the current invention;

FIG. 6 is a top view of the rigid spreader retractor of FIGS. 5A-5B with a soft tissue retractor in an open configuration;

FIGS. 8A-8B are distal and side views of legs of a rigid retractor according to an embodiment of the invention;

FIGS. 9A-9B are distal and side views of legs of a rigid retractor according to an embodiment of the invention;

FIGS. 10A-10C are distal, side, and side views, respectively, of a leg of a rigid retractor according to an embodiment of the invention;

FIGS. 11A-11C are distal, side, and side views, respectively, of a leg of a rigid retractor according to an embodiment of the invention;

FIGS. 12A-12C are distal, side, and side views, respectively, of a leg of a rigid retractor according to an embodiment of the invention;

FIGS. 13A-13C are distal, side, and side views, respectively, of a leg of a rigid retractor according to an embodiment of the invention;

FIG. 14 is a side view of an articulated arm according to an embodiment of the invention;

FIG. 16 is a cross-sectional view through the left side of a patient's heart showing a transapical procedure for implanting a prosthetic heart valve assisted by a rigid spreader retractor with soft tissue retractor according to an embodiment of the invention;

FIGS. 19-20 are perspective views, in closed and open configurations, respectively, of a rigid spreader retractor with articulated arm holding a heart valve ring and holder according to an embodiment of the invention.

DETAILED DESCRIPTION OF THE PREFERRED EMBODIMENTS

Figure 1:
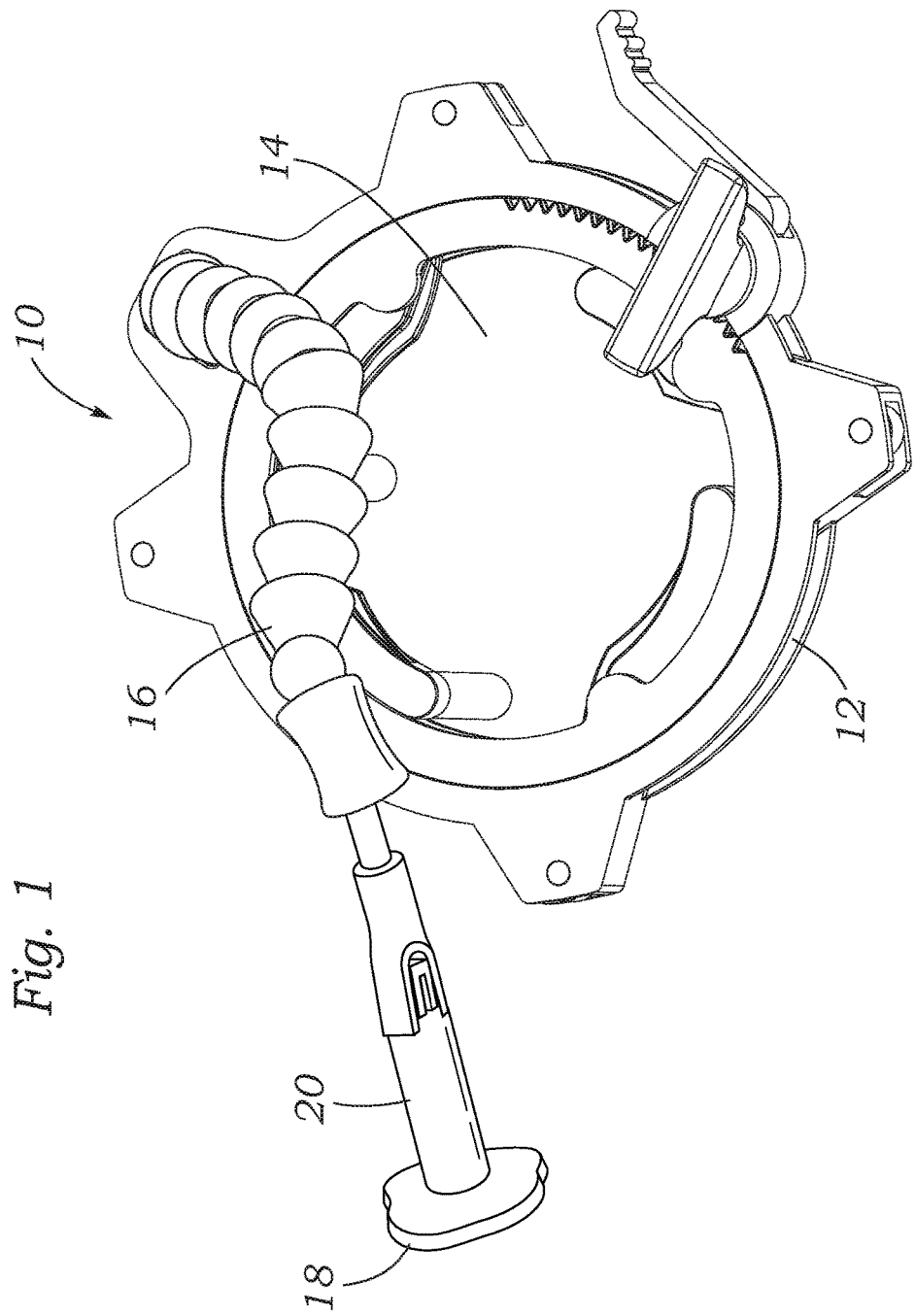
FIG. 1 is a top view of a retractor system shown with a single articulated arm and heart valve ring with holder according to an embodiment of the current invention.
Figure 2:
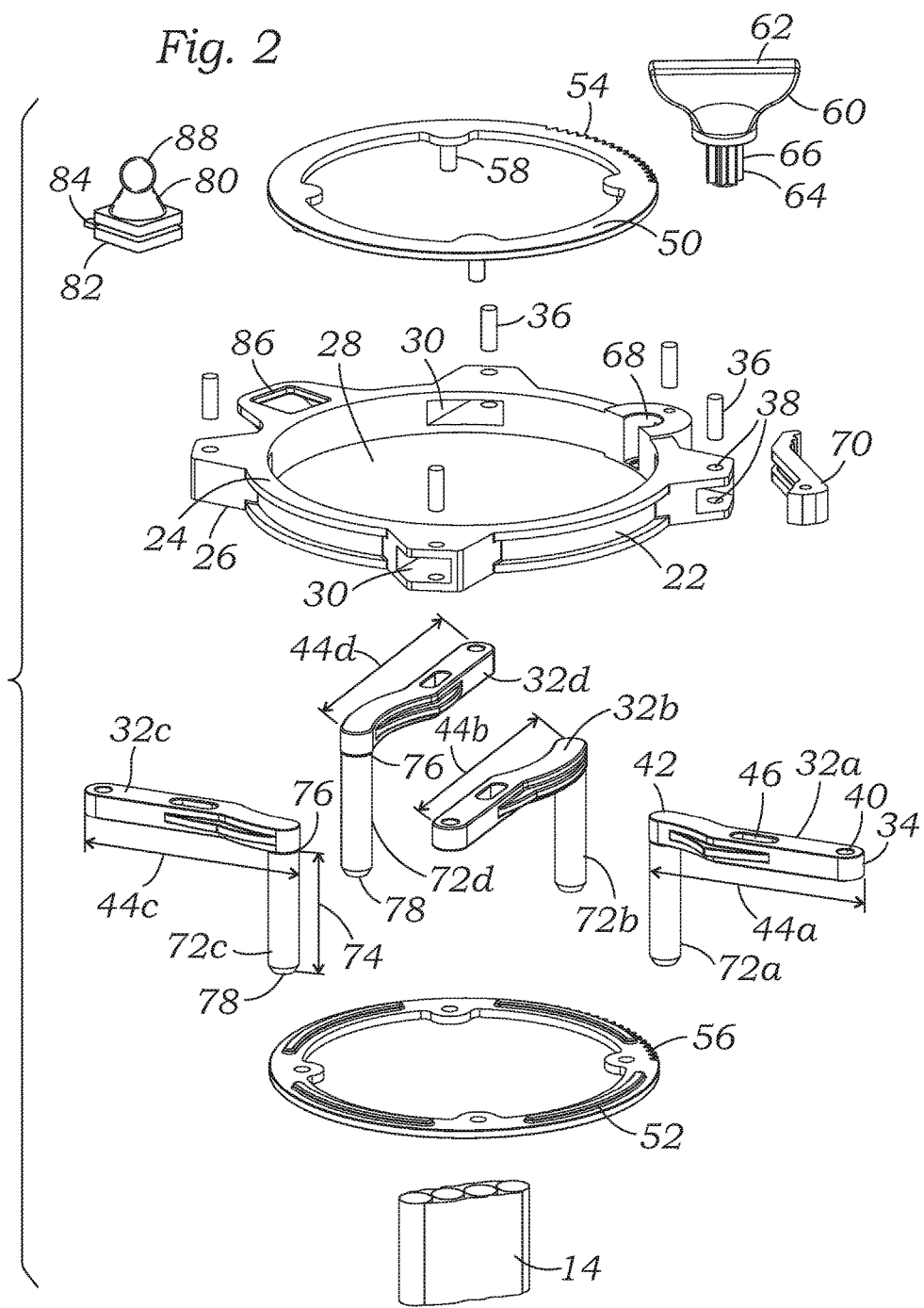
FIG. 2 is an exploded view of a rigid spreader retractor and soft tissue retractor according to an embodiment of the invention.

An exemplary embodiment of a tissue retractor system 10 is shown in FIG. 1 and essentially comprises a rigid spreader retractor 12, a soft tissue retractor 14, and an articulated arm 16. In the particular embodiment depicted, the arm 16 is holding a heart valve ring 18 via a heart valve ring holder 20. The retractor system 10 is capable of holding an incision or other body access point in an open position to provide visual access and/or physical access into a patient's body. For example, the retractor system may be used to provide physical access via an incision (e.g., an intercostal incision) for one or more tools (such as port-access devices), with the articulated arm configured to hold the tool(s) and provide stability thereto. As will be seen below, an exemplary form of the retractor is adapted to be advanced into a surgical/port incision or other access port into a human body and to spread the tissue outwardly to expand the incision to provide access therethrough.

As seen in FIGS. 2-4B, an exemplary rigid spreader retractor 12 is formed from a substantially circular main frame 22 having a top 24 and a bottom 26 and defining a substantially circular main frame central opening 28 (although other shapes, e.g., elliptical, square, rectangular, triangular, etc., for the opening and/or main frame are also within the scope of the invention). In a preferred embodiment, the main frame may define a lower surface with a slightly concave curvature that may conform to an outer surface of the patient adjacent the incision. The main frame may be formed from a single unitary piece of material, such as a single piece of metal and/or polymer, including materials formed from known techniques such as molding and/or machining. The main frame 22 includes a plurality of recesses 30.

A plurality of arms 32a-32d are positioned in the main frame central opening 28, with a proximal end 34 of each arm 32a-32d positioned in each of the inward-facing recesses 30. The arms 32a-32d are held in the recesses 30 via hinge posts 36 (which could be formed with screws or other connections) passing through frame hinge-point holes 38 and arm hinge-point holes 40. Each arm 34a-34d has a distal end 42, with a respective length 44a-44d from proximal end 34 to distal end 42. In each 32a-32d arm is a pivot slot 46 in a central portion thereof, running substantially parallel to the length of each arm.

An upper gear 50 and a lower gear 52 are positioned within the main frame central opening 28, with portions (e.g., proximal portions) of the arms 32a-32d sandwiched between the gears 50, 52. Each of the gears 50, 52 has a series of gear teeth 54, 56 extending at least partially along a circumference thereof. In the particular embodiment depicted, the series of gear teeth 54, 56 for each gear 50, 52 are on an outer circumferential portion of the gears 50, 52, although other positions for the gear teeth are also within the scope of the invention. The upper gear 50 and lower gear 52 are held together via a plurality of gear connecting posts 58 (and/or screws or similar connectors) which extend from upper gear 50 to lower gear 52 and also pass through the pivot slots 46 of the respective arms 32a-32d. The gears 50, 52 fit within the main frame central opening 28, and can rotate therewithin.

A rotation control knob 60 is rotatably secured to the main frame 22 at a control knob connection opening 68 formed at the side of the main frame central opening 28. The rotation control knob 60 includes a handle portion 62 and a knob gear 64 with gear teeth 66. The knob gear teeth 66 extend into contact with the gear teeth 54, 56 of the gears 50, 52, so that rotation of the control knob 60 causes a corresponding rotation of the gears 50, 52. A rotation control knob lock 70 has an unlocked position that permits the rotation control knob 60 to be rotated, and a locked position where the lock 70 prevents rotation of the rotation control knob 60.

Extending downwardly from each of the arms 32a-32d is a leg 72a-72d. The legs extend away from the main frame in a downward direction. Each leg 72a-72d has a length 74 from leg proximal end 76 to leg distal end 78. Different leg lengths are within the scope of the invention, with the particular leg length depending on the particular embodiment (including desired use, etc.). For example, a retractor for use in intercostal openings during, e.g., cardiac procedures, may have legs with lengths of between 1 and 3 inches.

Figure 3A:
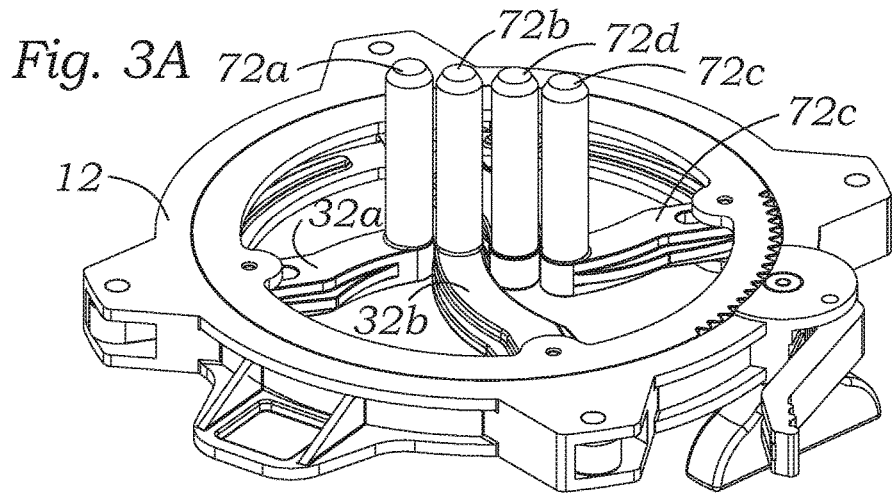
FIGS. 3A-3C are perspective views of a rigid spreader retractor in closed, partially open, and fully open configurations, respectively, according to an embodiment of the invention.
Figure 3B:
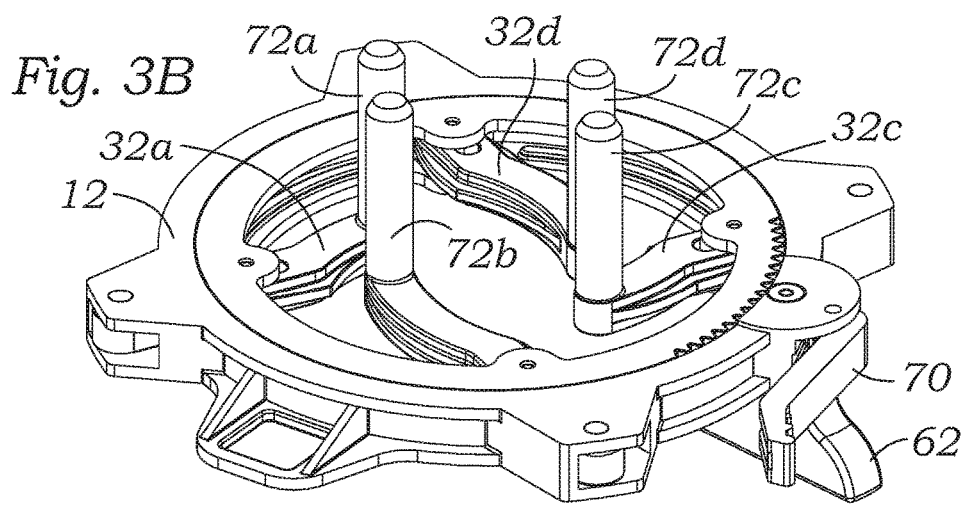
Figure 3C:
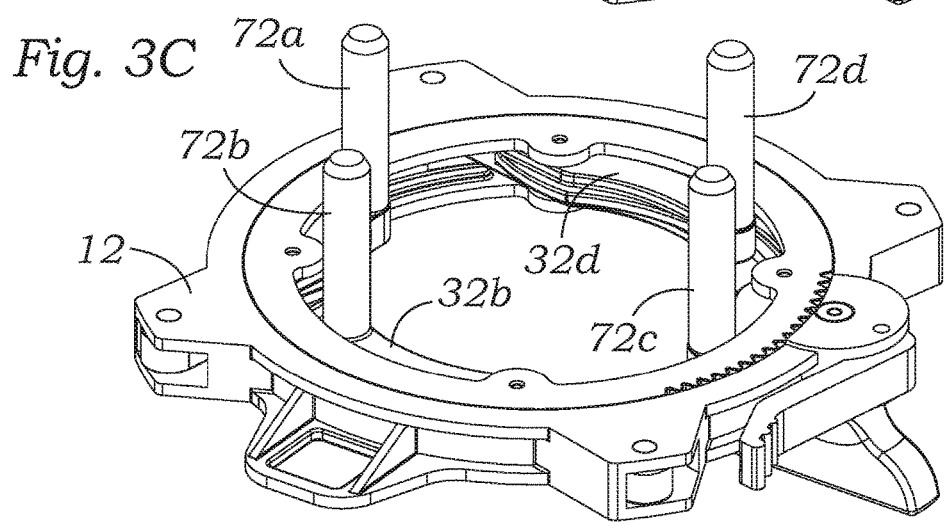

Due to the positioning of the gear connecting posts 58 within the arm pivot slots 46, rotation of the gears 50, 52 about the main frame central opening 28 causes corresponding hinge-like rotation of the arms 32a-32d about their respective hinge posts 36. This hinge-like rotation brings the arm distal ends 42 from a central/closed position (where the distal ends 42 are positioned toward the center of the main frame opening 28) to an open position (where the distal ends are moved outward to a position at or adjacent the outer perimeter of the main frame opening 28). In the assembled rigid retractor, rotation of the control knob 62 causes corresponding opening and closing of the arms 32a-32d and legs 72a-72d. The opening and closing of the arms 32a-32d and legs 72a-72d are depicted in FIGS. 3A-3C and 4A-4C, where FIGS. 3A and 4A depict the closed configuration, FIGS. 3B and 4B depict partially open, and FIGS. 3C and 4C depict fully open.

An arm support base 80 is secured to the main frame 22 via known methods to the main frame 22, such as via a removable snap-fit adaptor 82 (e.g., with adaptor release buttons 84) removably advanced and connected within an adaptor snap-fit opening 86 in the main frame 22. Pressing inwardly and/or downwardly on the adaptor release buttons 84 permits a user to slidingly remove the snap-fit adaptor 82 from the main frame 22. The arm support base 80 has an upper arm-receiving portion 88 configured to be secured to a flexible arm assembly (e.g., element 16 from FIG. 1).

Figure 4A:
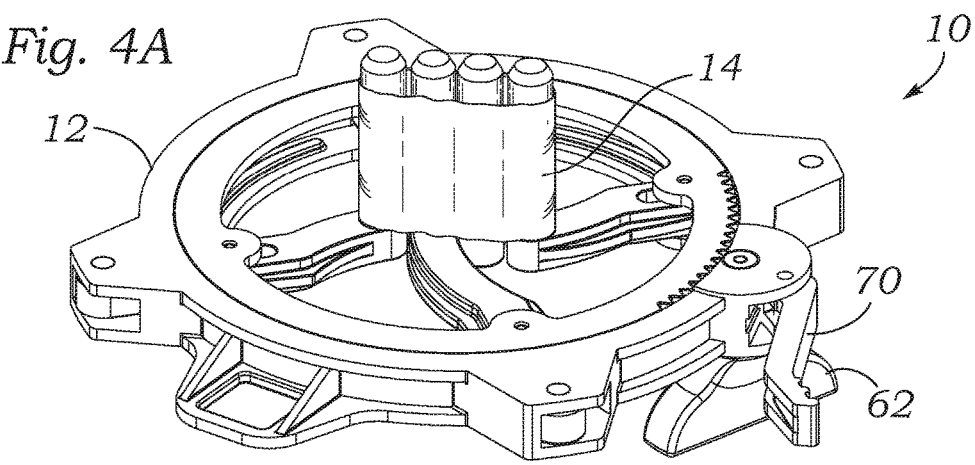
FIGS. 4A-4C are perspective views of a rigid spreader retractor with soft tissue retractor in closed, partially open, and fully open configurations, respectively, according to an embodiment of the invention.
Figure 4B:
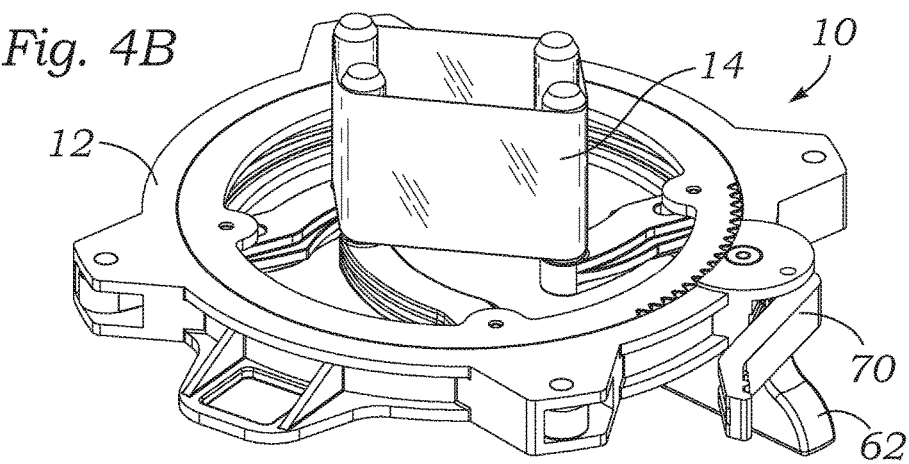
Figure 4C:
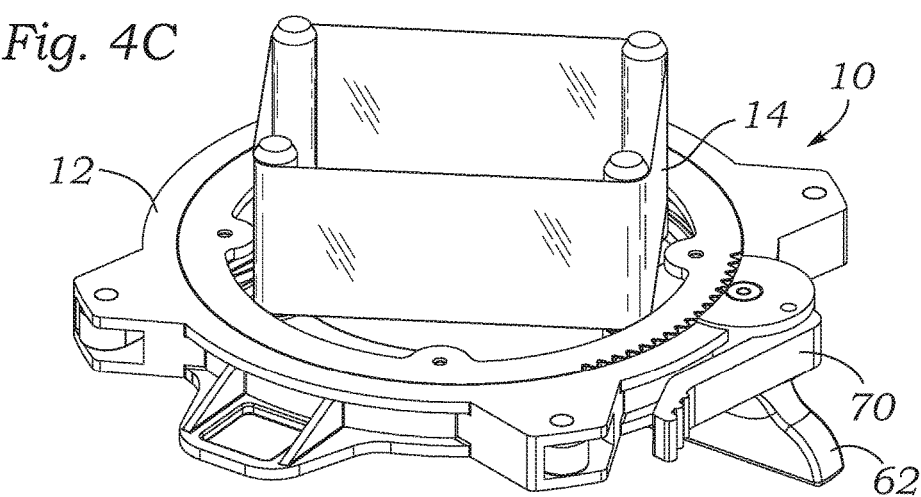
Figure 7A:
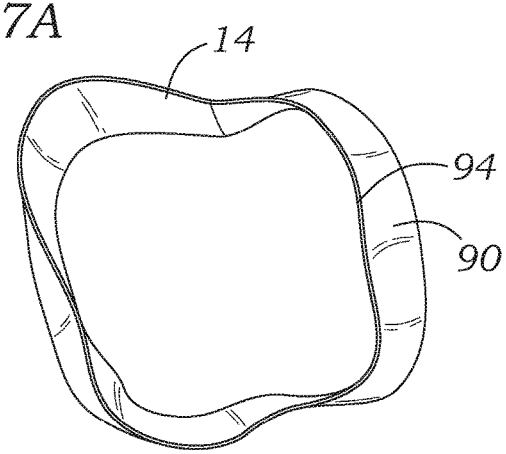
FIGS. 7A-7C depict top, side, and perspective views of a soft tissue retractor according to an embodiment of the invention.
Figure 7B:
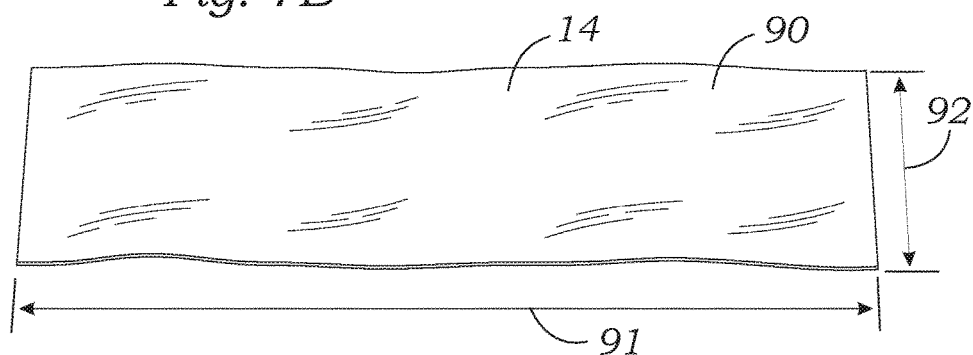
Figure 7C:
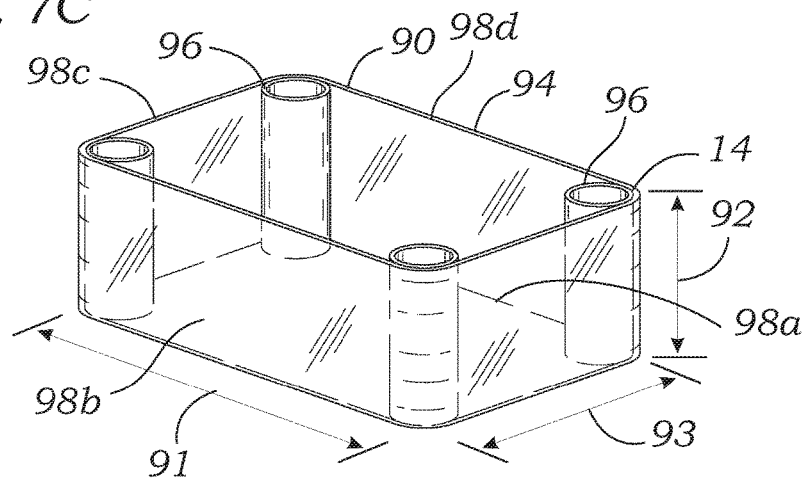

A soft tissue retractor 14 is configured to be slidingly positioned over and around the legs 72a-72d, as depicted in FIGS. 4A-4C. The soft tissue retractor 14, depicted more clearly in FIGS. 7A-7C, has a depth 92 and a perimeter 94. Note that FIG. 7A-7B depict the soft tissue retractor outer portion 90 without the leg-receiving pockets, while FIG. 7C depicts the complete soft tissue retractor 14 with pockets 96. As shown in FIG. 7C, the soft tissue retractor 14 includes one or more (e.g., four as depicted) leg-receiving pockets 96 which may substantially match the dimensions (e.g., shape, width, and/or length) of the rigid retractor legs. The perimeter 94 of the soft tissue retractor, and the positions of the leg-receiving pockets 96 positioned thereon, may match the outline and locations of the legs when the rigid retractor is in the open position. For example, for a rigid retractor such as in FIGS. 2-4B where the legs in the open configuration form a substantially non-square rectangular shape, the leg-receiving pockets are positioned about the perimeter of the soft tissue retractor so when the soft-tissue retractor is opened with leg-receiving pockets at corners thereof, the leg-receiving pockets form corners of a rectangular- (non-square) shape defined by the soft tissue retractor. Such an embodiment is depicted in FIG. 7C, where opposing sides (e.g., 98a and 98c, or 98b and 98d) are of equal length but adjacent sides are of different lengths. For a rigid retractor with "square" leg pattern such as the embodiment in FIGS. 5A-5B, the leg-receiving pockets of the soft tissue retractor would desirably form corners of a square-shape defined by the soft tissue retractor (e.g., where all sides of the soft tissue retractor are of equal length). The soft-tissue retractor thus should substantially match whatever shape is defined by the legs of the opened rigid retractor.

The soft tissue retractor may be formed from various materials, such as 3-5 mil polyurethane. The soft tissue retractor may preferably be formed from material which cannot stretch much at all so that inward pressure from soft tissue is strongly resisted. Alternatively, for stretchable material the material when tensioned in the open position should have sufficient strength to strongly resist any inward pressure from the soft tissue.

In an embodiment where opposing arms (e.g., 32a and 32c, or 32b and 32d) have equal lengths but adjacent arms have non-equal lengths, as depicted in FIGS. 3A-3C and 4A-4C, when the retractor is in the closed position the legs 72a-72d may align in a line toward the center of the frame central opening (as depicted in FIGS. 3A, 4A, 8A), which may make it easier to advance the line of legs into a lengthwise incision 100, as depicted in FIG. 8B. In the open configuration, the legs form a non-square rectangular pattern (and thus will form a substantially rectangular and non-square surgical access opening in the incision/other opening into the patient) about the circumference, as depicted in FIGS. 3C and 4C. In an embodiment where the arm lengths 44a-44d are essentially the same for all the arms 32a-32d, as depicted in FIGS. 5A-6, in the retractor closed position the legs may be bunched adjacent to each other in square pattern (FIGS. 5A-5B and 9A-9B), which may make it easier to advance the bunch of legs into a puncture-like opening 102, such as that formed via a trocar, as depicted in FIG. 9B. In the open configuration, the legs form a square pattern (and thus will form a substantially square surgical access opening when the retractor is opened in the incision/other opening into the patient) about the circumference, as depicted in FIGS. 6A-6D.

The legs 72a-72d may taper from their proximal ends 76 toward their distal ends 78, with the tapered distal ends 78 easing the advancement of the legs into an incision or other opening through which the retractor is advanced. Various tapers are within the scope of the invention. For example, the taper for all or some legs of a retractor of the invention may be centered to form a single center tip 104, as depicted in FIGS. 10A-C. The taper for all or some legs of a retractor of the invention may be toward a single tip 106 but toward one side of the leg, so that the distal tip is positioned toward one side of the leg (as opposed to being in the longitudinal center of the leg) as depicted in FIGS. 11A-C. The taper for all or some legs of a retractor of the invention may be centered to form a single line tip 108 extending across the distal end of the leg 72, as depicted in FIGS. 12A-C. The taper for all or some legs of a retractor of the invention may be toward a single line 110 but toward one side of the leg, so that the distal tip is positioned toward one side of the leg (as opposed to being in the longitudinal center of the leg) as depicted in FIGS. 13A-C. For example, in the embodiment of FIGS. 5A-5B, the tapers may be positioned to one side of each leg in similar fashion to FIGS. 11A-C above) in such a way that when the retractor is in the closed position with the legs centered together, the tapers of the legs are positioned adjacent to each other in the centermost portion of the leg "bundle", thus forming a leg bundle that has an overall tapered profile, as depicted in FIGS. 9A-9B. Such a profile may make it easier to advance the legs into a puncture-like opening 102 in the patient as depicted in FIG. 9B. Similarly, in an embodiment such as that depicted in FIGS. 8A-8b where the legs are in a line when in the closed position, the legs 72a, 72c may taper as in FIGS. 11A-11C, with the taper point positioned on the side closest to the adjacent legs 72b, 72d. The inward legs 72b, 72d may taper as in FIGS. 12A-12C, with the taper line of the tips aligned with the line defined by the adjacent legs 72a-72d as depicted in FIGS. 8A-8B for ease of advancement into a lengthwise incision 100.

Elements of the rigid retractor 12, e.g., the main frame, gears, arms, legs, etc., may be formed from various materials, including metals and/or polymers and/or ceramics or combinations thereof. Examples of materials include stainless steel, aluminum, ULTEM, PEEK (polyetheretherketone—which may be reinforced with glass fibers, e.g., 20% by weight glass fibers), Acrylonitrile-Butadiene-Styrene (ABS), and other materials. Note that different elements may be formed from different materials from the other elements. For example, the main frame may be formed from somewhat softer materials than the retractor arms/legs and/or retractor posts. Depending on the particular embodiment, some or all of the elements may be formed from non-radiopaque materials for improved imaging ability during procedures using X-ray imaging.

The articulated arm 16 may be provided in a number of different forms that provide rigidity or stability to an implement, such as a valve ring/valve ring holder and/or prosthetic heart valve/prosthetic heart valve holder/catheter, while also enabling easy manipulation to reposition the implement. Articulated arms are well known in the art, and the illustrated embodiment includes a plurality of linked segments 120 that are coupled to each other through a ball joint or other similar three-dimensional structural connection. Of course, a simple malleable arm may also be used with some loss of fine control, but the purpose of three-dimensional variation remains. In short, the illustrated articulated arm 16 is shown as an example only, and many variations are possible. In a preferred embodiment, adjustments can be made to the articulation/positioning arm 16 at any time without a loosening/locking mechanism. Furthermore, one such an articulated arm 16 may be used in some of the embodiments of retractors/procedures disclosed herein, with two or more arms provided for other embodiments of retractors/procedures for greater stability as described below.

The articulated arm 16 has a proximal end 122 which is depicted snapped onto the upper arm-receiving portion of the arm support base 80, which can itself be snapped onto the main frame base of the rigid retractor. The arm 16 comprises segments 120 that may snap together, with each contributing a compressive force against adjacent segments to maintain constant friction. This friction between segments gives the arm 16 its ability to resist radial, axial, and rotational movement when external forces are less than its frictional limit, but allows movement of the arm when the frictional force is exceeded. Each segment 120 is free to rotate relative to adjacent segments about their common axes. A lumen (not shown) extending down the middle of the arm can house electrical wires for powering a component at the distal end 124 thereof and/or house a malleable rod down the center of the elements, which may provide enhanced resistance to external forces, and provide improved stabilization. Typically, the segments 120 may be made of a polyester material.

The arm distal end 124 is preferably configured to grasp an implement and hold it in position during a surgical procedure. For example, in the embodiment depicted, the arm distal end 124 includes a snap fitting 126 configured to removably hold the handle of a valve ring holder such as the holder 20 depicted in FIG. 1. Other embodiments of arm distal ends 124 may include a stabilizing cuff-like structure or adjustable vise-like structure configured to grasp implements, such as catheters, etc. The element configured to grasp the implement may provide some give to its capture of the implement, both securing it and permitting it to move into different angles.

Figure 15A:
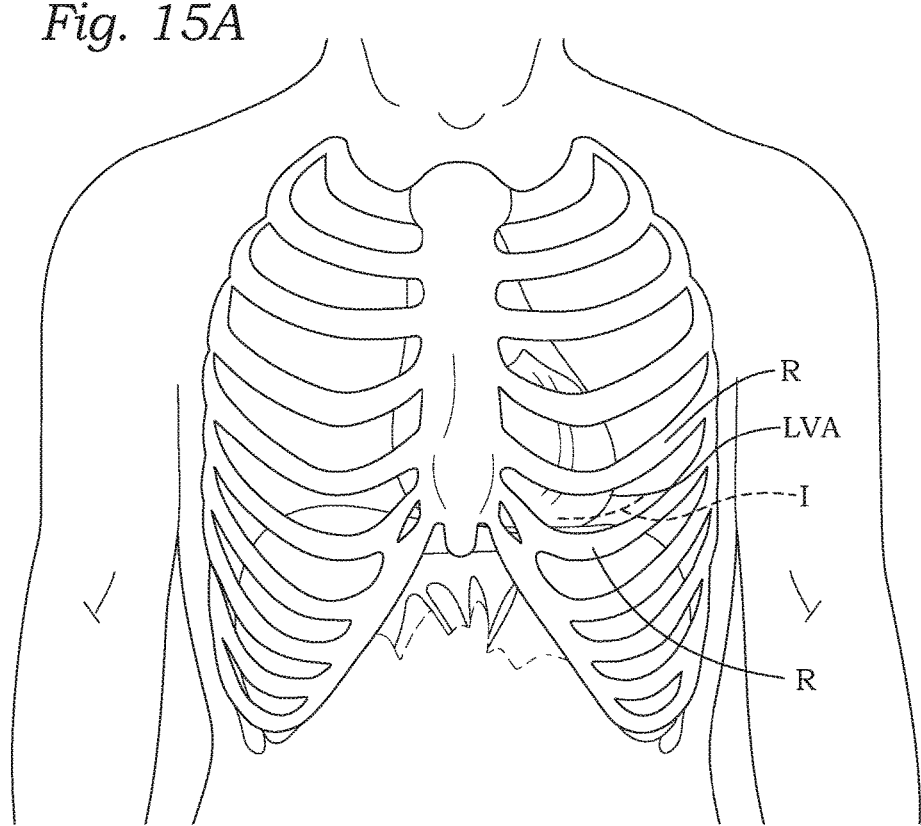
FIG. 15A is a schematic frontal view of a patient showing the location of an intercostal incision providing access to the apex of the left ventricle of the heart.
Figure 15B:
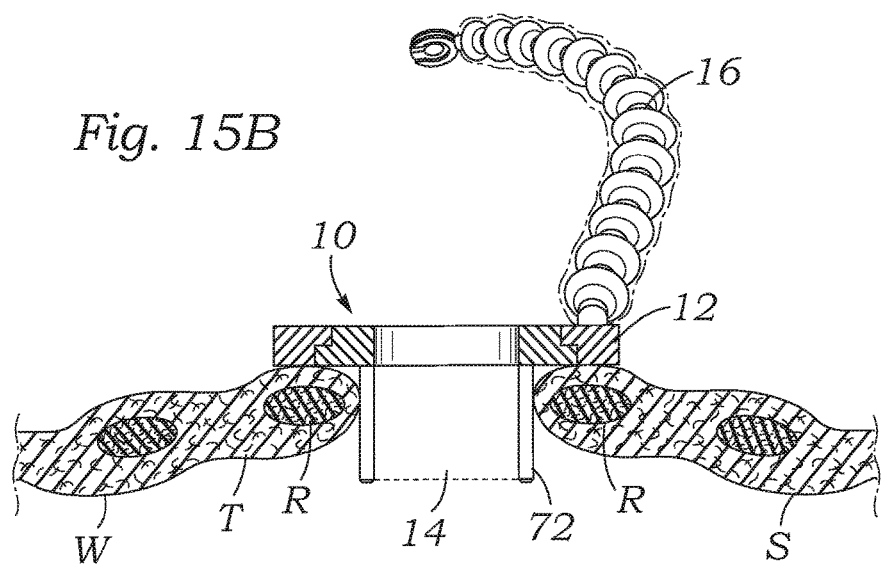
FIG. 15B is a cross-sectional view of a patient's chest wall showing a rigid spreader retractor with soft tissue retractor deployed through an intercostal incision according to an embodiment of the invention.

FIGS. 15A and 15B illustrate the use of an exemplary retractor system 10 during an intracardiac surgical procedure carried out with an implement in the form of a heart valve ring 18 and valve ring holder 20 through an intercostal incision I in a chest wall CW. As depicted in FIG. 15A, an intercostal incision I is formed between adjacent ribs R. The legs 72 of the rigid retractor 12, with soft tissue retractor 14 thereon, are advanced into the incision I. The rigid retractor 12 is expanded to the open configuration, so that the rigid retractor legs 72 hold the ribs apart and the soft tissue retractor 14 holds the soft tissue back, thereby creating an access and/or visualization opening for the surgeon or other medical personnel to use.

The main frame base 22 is held generally parallel to the chest wall CW such that the articulated arm 16 initially projects perpendicularly away therefrom. The base 22 may preferably be contoured to accommodate the shape of the patient's surface anatomy, such as having a concave lower surface. Due to the high degree of malleability and rotatability of the arm 16, the implement holder 126 may be positioned and angled in a desired way to optimally receive and hold the desired implement. The retractor base 22 thus provides a firm yet resilient support for the implement, holding it at a desired position/angle for the particular surgery.

The arm 16 can be articulated into a position that accommodates the natural angle of the implement and the patient's anatomy, and the implement can then be constrained, for example "snapped," into the implement holder of the arm 16. Adjustments can be made to the articulation/positioning at any time, without a loosening/locking mechanism.

As mentioned, the retractor system 10 may be used for a number of procedures, but is particularly well-suited for stabilizing an implement such as a heart valve ring holder or prosthetic heart valve holder/introducer sheath for intracardiac surgery. One surgical procedure that utilizes the devices of the present application is a transapical heart valve replacement through the left ventricular apex, as disclosed in U.S. application Ser. No. 12/821,628, filed Jun. 23, 2010, the disclosure of which is expressly incorporated herein. First, the prosthetic heart valve and various delivery instruments are selected and prepared for use by removing them from any packaging and rinsing or sterilizing as needed. A prosthetic heart valve 134 is then crimped over a balloon 136 on a catheter 138.

An intercostal incision I in the chest wall CW between two ribs R and over the left ventricular apex LVA is created, as was depicted in FIG. 15A. The rigid retractor legs 72 and soft tissue retractor 14 may be advanced into and expanded within the intercostal incision I to hold back the tissue surrounding the incision I, thus enhancing access and visibility to the left ventricular apex LVA.

Next, as seen in FIG. 16, the surgeon may install one or more purse-string sutures 140 in the tissue of the left ventricular apex LVA of the heart 144 prior to formation of an initial puncture in the heart wall. In a preferred embodiment, the surgeon places a first line of purse-string sutures generally in a first circle in one direction, and then places a second line of purse-string sutures generally in a circle concentric to the first circle but in an opposite direction. The result is two concentric circles of separate purse-string sutures defining a periphery within which the puncture is formed. The purse-string sutures 140 can therefore be pulled to cinch the ventricular tissue around whatever object passes through the puncture. In particular, the purse-string sutures are tightened around both a guidewire and introducer sheath 130.

The surgeon introduces a guidewire through a pre-formed apical puncture in the left ventricle LV and within the purse string sutures, through the native aortic valve AV and into the ascending aorta AA. A pre-dilation step of the annulus may be performed to enlarge or crack existing calcification in the aortic annulus. The surgeon then inserts a dilator and introducer sheath 130 into the LV through the apical puncture as an access port.

At this point the introducer sheath 130 may be secured in place via the holder 132 (such as the cuff-like holder depicted) and the arm 16 of the retractor system 10 of the current invention. The surgeon can adjust the placement of the arm 16 and introducer sheath 130 until a desired placement of the introducer sheath is achieved.

The balloon catheter is advanced over the guidewire and through the introducer sheath 130. The surgeon locates the prosthetic heart valve 134 at the aortic annulus and between the native aortic leaflets. Radiopaque markers may be provided on the distal tip of the introducer sheath to more accurately determine its position relative to the valve and balloon. When the surgeon is satisfied of the proper positioning and rotational orientation of the valve, as seen in FIG. 13, the balloon 136 is expanded into contact with the annulus, thus deploying the heart valve 134 at the desired position in the annulus.

The surgeon then deflates the balloon 136 and withdraws the entire delivery system including the balloon catheter over the guidewire. The introducer sheath 130 is withdrawn, followed by the guidewire. Ultimately, the purse-string sutures previously described are cinched tight and tied to close the puncture.

A single-arm retractor has been described as one embodiment of the invention. However, retractors with multiple arms are also within the scope of the invention.

Figure 17:
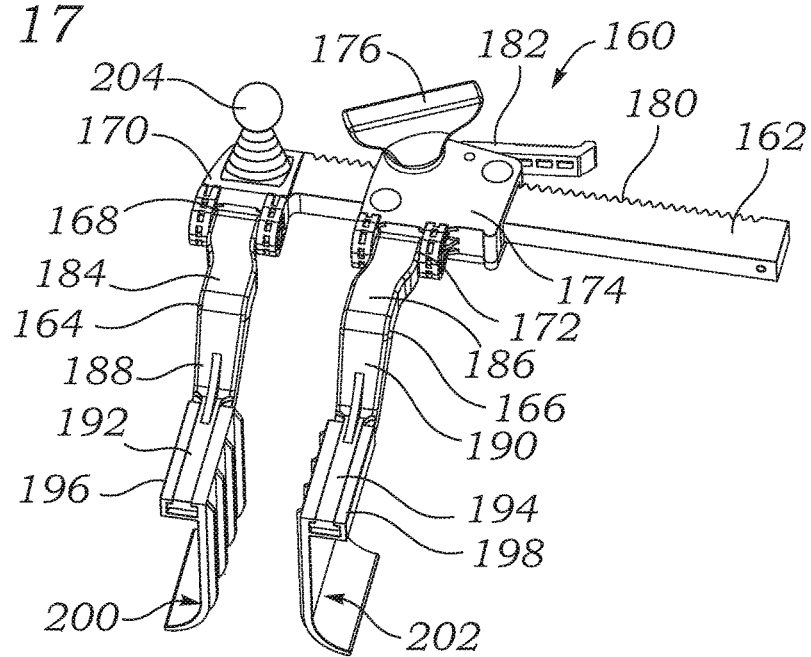
FIG. 17 is a perspective view of a rigid spreader retractor according to an embodiment of the invention.

FIG. 17 depicts a disposable retractor 160 according to an embodiment of the invention. The disposable retractor 160 comprises a rack 162, a fixed arm 164, and a movable arm 166. The fixed arm 164 is rotatably secured via a hinge-like connection 168 to the base end 170 of the rack 162. The movable arm 166 is rotatably secured via a hinge-like connection 172 to a car 174 movably secured to the rack 162. The car 174 includes a control knob 176 which, when rotated, causes a gear 178 on the lower part of the knob to engage teeth 180 on the rack and thereby effectuate controlled movement of the car 174 along the rack 162. Movement of the car 174 along the rack 162 causes corresponding movement the movable arm 166 with respect to the fixed arm 164. A lock 182 is provided which can, when in the locked position, prevent movement of the car 174 along the rack 162.

In the particular embodiment depicted, the fixed and movable arms 164, 166 each have a proximal portion 184, 186, an intermediate portion 188, 190, and a distal portion 192, 194. The proximal portion 184 of the fixed arm 164 is substantially parallel to the distal portion of that same arm. The intermediate portion 188 of the fixed arm 164 is angled with respect to the proximal portion 184 and distal portion 192 by an angle of between 30 and 60 degrees. Similarly, the proximal portion 186 of the movable arm 166 is substantially parallel to the distal portion of that same arm, while the intermediate portion 190 of the movable arm 166 is angled with respect to the proximal portion 186 and distal portion 194 by an angle of between 30 and 60 degrees. Removable paddles 196, 198 are connected, such as via sliding and/or snap connection, to the distal portion 192, 194 of the arms 164, 166. Each paddle 196, 198 includes a blade 200, 202 configured to be advanced into an incision and to engage and hold back tissue when the arms are spread apart.

Figure 18:
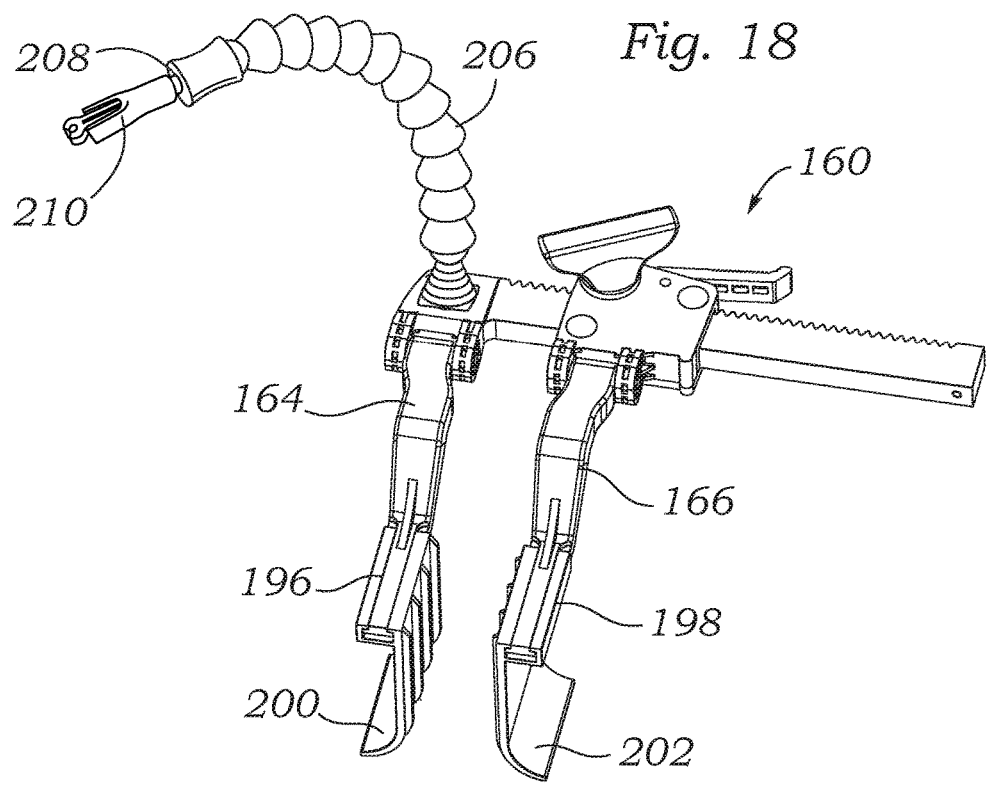
FIG. 18 is a perspective view of a rigid spreader retractor with articulated arm according to an embodiment of the invention.
Figure 21:
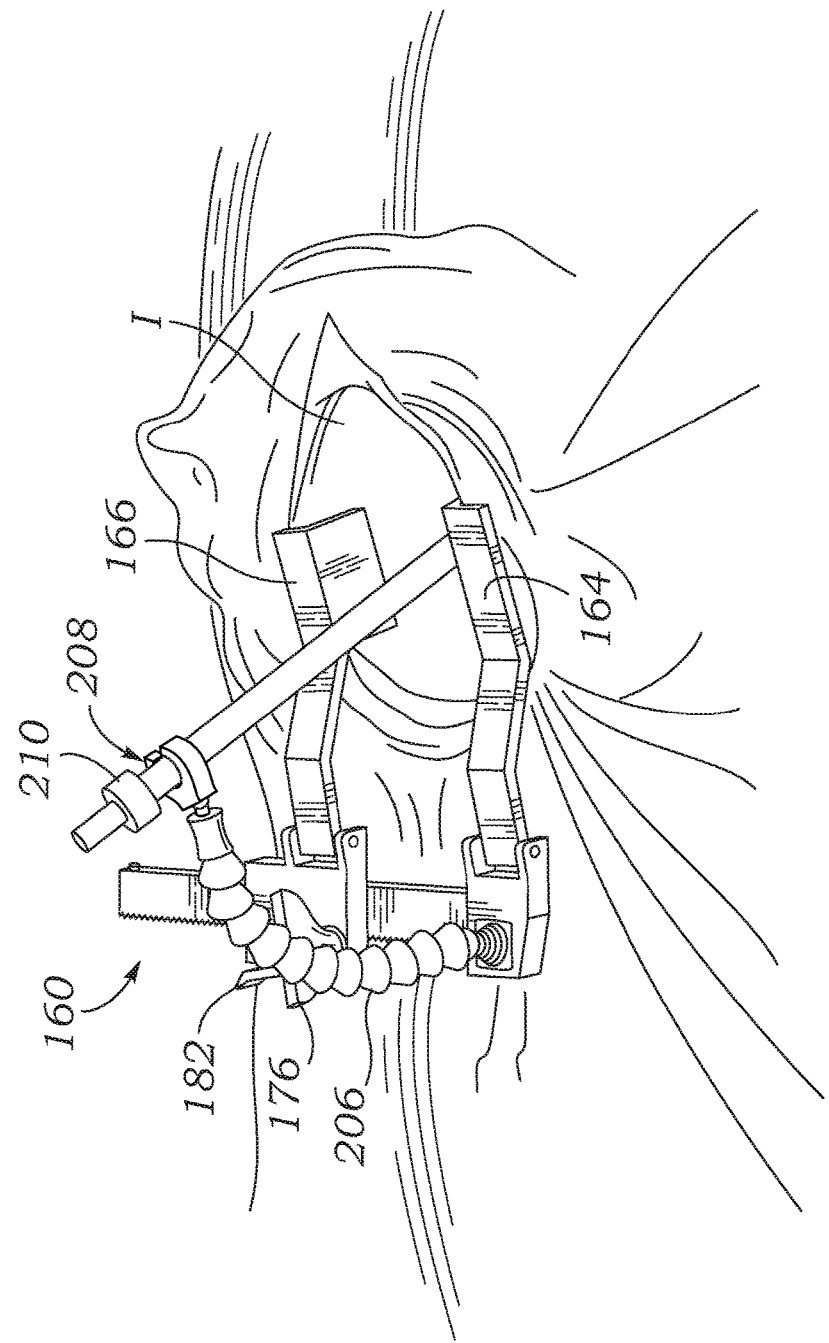
FIG. 21 is a perspective view of a surgical procedure carried out with a rigid spreader retractor through an intercostal incision according to an embodiment of the invention.

The retractor 160 has an arm attachment 204, which in the particular embodiment is positioned at the base end of the rack (although other positions are also within the scope of the invention. The arm attachment 204 is configured to receive and hold, such as via a snap-on connection, an articulated arm 206 similar (or even identical) to that depicted and described as element 16 in FIGS. 1 and 14-16. The articulated arm 204, depicted in FIGS. 17-18, has a distal end 208 having an implement-grasping mechanism 208, which in the particular embodiment depicted is a snap-on piece configured to engage and hold a valve ring holder 20 and valve ring 18 as depicted in FIGS. 19-20. As depicted in FIG. 19, the retractor in the closed position has its fixed and movable arms, and according the blades and paddles, relatively close together. To open the retractor (and thus open an incision in which the paddles/blades are placed), a user rotates the control knob 176 to move the movable arm 166 and associated paddle 198 and blade 202 away with respect to the fixed arm 164 and associated paddle 196 and blade 200, as depicted in FIG. 20. As depicted in FIG. 21, the retractor 160 can be used to hold open an incision I while simultaneously holding and stabilizing an implement such as a catheter 210. The spreader 160 can thus hold open adjacent ribs to form an aperture through which the catheter 210 and other surgical instruments (not shown) may be passed.

In the particular embodiment depicted, all elements of the retractor (except potentially small components such as hinge pins) may be non-radiopaque. Moreover, the elements of the retractor may be formed form relatively inexpensive materials so that the entire retractor can be disposed of after use. For example, ULTEM and/or PEEK, both of which may have glass fibers added (e.g., 20%, 30% fiber glass by weight) for improved strength, may be used to form all or portions of the rigid retractor.

While the invention has been described in its preferred embodiments, it is to be understood that the words which have been used are words of description and not of limitation. Therefore, changes may be made within the appended claims without departing from the true scope of the invention.

What is claimed is:

1. A device for surgical retraction to create an opening in a patient, comprising:
    a main frame comprising a main frame proximal side and a main frame distal side, the main frame further comprising a central opening passing from the main frame proximal side to the main frame distal side, the main frame comprising an outer structure surrounding the central opening;
    a plurality of movable arms extending from the outer structure and into the central opening, each movable arm comprising an arm proximal end connected to the outer structure and an arm distal end positioned in the central opening;
    a plurality of legs, wherein one of said plurality of legs extends from each of the plurality of movable arms, wherein each of said plurality of legs comprises a leg proximal end secured to one of the plurality of movable arms, and each of said plurality of legs comprises a leg distal end, wherein each of said plurality of legs extends distally from the main frame distal side;
    wherein the device comprises a closed configuration wherein the plurality of movable arms extends into the central opening and the plurality of legs are positioned toward a center portion of the central opening with the plurality of legs adjacent each other with the leg distal ends forming a substantially straight line therebetween when viewed from the main frame distal side, the device further comprising an open configuration wherein the plurality of movable arms are moved so that the arm distal ends are positioned at or adjacent an outer perimeter of the central opening with each of the plurality of legs spaced apart from the other legs so that the plurality of legs define a periphery having a polygonal shape, wherein each of the plurality of legs defines a corner of the polygonal shape.

2. The device of claim 1, wherein each of the plurality of legs tapers toward the leg distal end.

3. The device of claim 2, wherein in the closed configuration the plurality of legs comprises a first end leg at a first end of the substantially straight line, a second end leg at a second end of the substantially straight line, and one or more intermediate legs positioned in the substantially straight line between the first end leg and the second end leg, wherein the first end leg is tapered toward a side of the leg distal end of the first end leg, the second end leg is tapered toward a side of the leg distal end of the second end leg, and wherein each intermediate leg is tapered toward a center line at the leg distal end of the intermediate leg, wherein in the closed configuration the center line of each intermediate leg is parallel to the substantially straight line formed by the leg distal ends.

4. The device of claim 1, wherein the polygonal shape comprises a rectangle.

5. The device of claim 1, wherein each leg comprises a substantially circular profile when viewed from the leg distal end.

6. The device of claim 1, wherein each leg comprises a length between 1 and 3 inches.

7. The device of claim 6, further comprising:
    a soft tissue retractor secured to the plurality of legs, the soft tissue retractor comprising a flexible film extending between the plurality of legs and around the periphery defined by the plurality of legs, wherein the soft tissue retractor comprises a plurality of tubes connected by the flexible film, wherein each of the plurality of tubes is slidingly disposed over a corresponding one of the plurality of legs.

8. A surgical retractor, comprising:
    a base; and
    a plurality of legs extending downwardly from the base, wherein each of the plurality of legs comprises a length extending from a leg proximal end to a leg distal end;
    wherein the plurality of legs are secured to the base via an assembly configured to move the plurality of legs from a first configuration where the leg proximal ends are adjacent each other in a substantially central position on the base with the leg distal ends aligned with each other in a substantially straight line, to a second configuration where the leg proximal ends are spaced apart from each other and in a substantially non-central position on the base such that the plurality of legs define a periphery of an open space therebetween.

9. The surgical retractor of claim 8, wherein in the first configuration and in the second configuration the plurality of legs are parallel to one another.

10. The surgical retractor of claim 8, further comprising:
    an implement arm attached to and extending away from the base and capable of being bent into and retaining a variety of shapes; and
    an implement holder secured to a distal end of the implement arm.

11. The surgical retractor of claim 10, wherein the implement holder comprises a holder cuff or a distal clip adapted to hold a part of an implement.

12. The surgical retractor of claim 8, wherein the length of each of the plurality of legs is between 1 and 3 inches.

13. The surgical retractor of claim 8, further comprising:
a soft tissue retractor secured to the legs, the soft tissue retractor comprising a flexible film extending between the legs and around the periphery defined by the plurality of legs, wherein the soft tissue retractor comprises a substantially continuous loop of flexible film, the substantially continuous loop defining a soft tissue retractor perimeter.

14. The surgical site retractor of claim 13, wherein the length of each of the plurality of legs is between 1 and 3 inches, and wherein the soft tissue retractor comprises a soft tissue retractor depth of between 1 and 3 inches.

15. A surgical retractor, comprising:
a base configured to be positioned against an exterior chest wall of a patient;
a plurality of legs extending downwardly from the base, wherein each of the plurality of legs comprises a length extending from a leg proximal end to a leg distal end of the leg, wherein the length is between 1 and 3 inches; and
an expansion mechanism configured to move the plurality of legs from a closed configuration on the base wherein the plurality of legs are parallel to and adjacent each other and align with each other in a straight line toward a center of the base, to an open configuration where the plurality of legs are parallel to and spaced apart from each other and defining a periphery of an open space therebetween.

16. The surgical retractor of claim 15, wherein each of the legs is tapered from the leg proximal end to the leg distal end.

17. The surgical retractor of claim 15, wherein the plurality of legs comprises a first end leg at a first end of the straight line, a second end leg at a second end of the straight line, and one or more intermediate legs positioned in the straight line between the first end leg and the second end leg.

18. The surgical retractor of claim 17, wherein the first end leg is tapered toward a side of the leg distal end of the first end leg, and the second end leg is tapered toward a side of the leg distal end of the second end leg, wherein each intermediate leg is tapered toward a center line at the leg distal end of the intermediate lag, wherein when the plurality of legs are in the closed configuration the center line is parallel to the straight line formed by the plurality of legs toward the center of the base.

19. The surgical retractor of claim 15, further comprising:
a soft tissue retractor secured to the plurality of legs, the soft tissue retractor comprising a flexible film extending between the plurality of legs and around the periphery defined by the plurality of legs.

20. The surgical retractor of claim 19, wherein each of the plurality of legs comprises a substantially circular profile when viewed from the leg distal end of the respective leg, and wherein the soft tissue retractor comprises a plurality of tubes connected by the flexible film, and wherein each of the plurality of tubes is slidingly disposed onto a corresponding one of the plurality of legs.

* * * * *